US008790654B2

(12) United States Patent
Galli

(10) Patent No.: US 8,790,654 B2
(45) Date of Patent: Jul. 29, 2014

(54) GLYCOSYLCERAMIDE ADJUVANT FOR SACCHARIDE ANTIGENS

(75) Inventor: Grazia Galli, Florence (IT)

(73) Assignee: Novartis AG, Basel (CH)

( * ) Notice: Subject to any disclaimer, the term of this patent is extended or adjusted under 35 U.S.C. 154(b) by 1408 days.

(21) Appl. No.: 11/662,371

(22) PCT Filed: Sep. 7, 2005

(86) PCT No.: PCT/IB2005/002788
§ 371 (c)(1),
(2), (4) Date: Apr. 8, 2008

(87) PCT Pub. No.: WO2006/027685
PCT Pub. Date: Mar. 16, 2006

(65) Prior Publication Data
US 2008/0199487 A1    Aug. 21, 2008

(30) Foreign Application Priority Data

Sep. 7, 2004  (GB) .................................. 0419846.1

(51) Int. Cl.
*A61K 39/385* (2006.01)
(52) U.S. Cl.
USPC .................................. 424/193.1; 424/197.11
(58) Field of Classification Search
None
See application file for complete search history.

(56) References Cited

U.S. PATENT DOCUMENTS

| 7,273,852 | B2 | 9/2007 | Tsuji et al. | |
| 7,488,491 | B2 | 2/2009 | Tsuji et al. | |
| 2003/0157135 | A1* | 8/2003 | Tsuji et al. | 424/278.1 |
| 2005/0192248 | A1 | 9/2005 | Tsuji et al. | |
| 2008/0220010 | A1 | 9/2008 | Telford et al. | |
| 2009/0304743 | A1 | 12/2009 | Galli | |

FOREIGN PATENT DOCUMENTS

| AU | 748716 | * 12/1998 |
| WO | 98/51339 | * 11/1998 |
| WO | WO 02/058737 A2 | 8/2002 |
| WO | WO 03/009812 | 2/2003 |
| WO | WO 2004/032958 | 4/2004 |
| WO | WO 2005/000348 | 1/2005 |
| WO | WO2005/028618 | 3/2005 |
| WO | WO 2006/026389 | 3/2006 |
| WO | WO 2006/027685 | 3/2006 |
| WO | WO2006/027685 | 3/2006 |

OTHER PUBLICATIONS

Ahamad et al, New Vaccines and New Vaccine Technology 13(1):113-133, 1999.*
Austrian (Reviews of Infectious Diseases, vol. 11, supplement 3, p. S598-602, May-Jun. 1989.*
Buschard K., et al., "Sulphatide and its Precursor, Galactosylceramide , Influence the Production of Cytokines in Human Mononuclear Cells," Diabetologia, Berlin, DE, vol. 40, Suppl. 1, p. A89 (1997).
Snippe H., et al., Liposomes in Immunology, in Microspheres, Microcapsules and Liposomes; Arshady, R., Ed.; Citrus Book: London, vol. 2, pp. 503-523 (1999).
Mahanty et al., "Progress in the development of recombinant and synthetic blood-stage malaria vaccines,"The Journal of Experimental Biology, 206, 3781-3788 (2003).
Schijns, "Activation and programming of adaptive immune responses by vaccine adjuvants,"Veterinary Sciences Tomorrow (2001).
Ko S. et al. "Alpha-galactosylceramide can act as a nasal vaccine adjuvant inducing protective immune response against . . . " Journal of Immunology, 175(5): 3309-3317 (2005).
Van Kaer, L. et al. "Innate Immunity: NKT Cells in the Spotlight," Current Biology, 15(11): R429-R431 (2005).
Yu, K. et al. The diverse functions of CD1d-restricted NKT cells and their potential for immunotherapy, Immunology Letter, 100(1): 42-55 (2005).
Kawakami, K. et al. "Critical role of Valpha14+ natural killer T cells and their phase of host protection against . . . " Eur. J. Immunol., 33(12): 3322-3330 (2003).
Gonzalez-Aseguinolaza, G. et al. "Alpha-galactosylceramide-activated Valpha14 natural killer T cells mediate protection against murine malaria," PNAS, 97(15): 8461-8466 (2000).
Minagawa, S. et al. "Alpha-galactosylceramide mediates clearance of bacteria in murine . . . " Journal of Urology, 173(6): 2171-2174 (2005).
Maione, D. et al. "Identification of a universal group B Streptococcus vaccine by multiple genome screen," Science, 309(5731): 148-150 (2005).
Charles River Breeding Laboratories. "BALB/c Mice," Unknown [Online] Retrieved from the Internet: URL:http://www.criver.com/flex-content-area-documents-rm-rm-c-BALB-c-mice.pdf.
Haile, M. et al. "Immunization with heat-killed *Mycobacterium bovis* bacille Calmette-Guerin (BCG) in Eurocine(TM) L3 adjuvant protects . . . " Vaccine, 22(11-22): 1498-1508 (2004).
Wijnhoven, S. et al. "Accelerated aging pathology in ad libitum fed Xpd<TTD> mice is accompanied by features suggestive of caloric . . . " DNA Repair, 4(11): 1314-1324 (2005).
Numata, Y. et al. "Repeated Stimulation of Natural Killer T (NKT) Cells is Effective for Primary Sclerosing Cholangitis . . . " AASLD Abstracts, 126(4): A671, Abstract 171 (2004).
Miyamoto et al., "A Synthetic Glycolipid Prevents Autoimmune Encephalomyelitis by Inducing $T_H2$ Bias of Natural Killer T Cells," Nature, 413:531-534 (2001).
Schuchat, "Group B *Streptococcus*," The Lancet, 353:51-56 (1999).
Gupta et al., "Adjuvants for Human Vaccines-Current Status, Problems and Future Prospects," Vaccine, 13:1263-1276 (1995).
Workshop Summary Aluminum in Vaccines, Conference Report, Vaccine, 20:S1-S4 (2002).

(Continued)

*Primary Examiner* — Patricia A Duffy
(74) *Attorney, Agent, or Firm* — Helen Lee; Otis Littlefield

(57) ABSTRACT

The invention provides compositions and kits comprising: (a) a saccharide antigen conjugated to a carrier; and (b) an alpha-glycosylceramide adjuvant. The invention further provides uses of the compositions. It has been found that suppression of anti-saccharide immune responses by alpha-glycosylceramides can be reversed by conjugating the saccharide to a carrier.

11 Claims, 5 Drawing Sheets

(56) References Cited

OTHER PUBLICATIONS

Hunter, "Overview of Vaccine Adjuvants: Present and Future," Vaccine, 20:S7-S12 (2002).

Granoff et al., MF59 Adjuvant Enhances Antibody Responses of Infant Baboons Immunized with *Haemophilus influenzae* Tybe b and *Neisseria meningitidis* Group C Oligosaccharide-$CRM_{197}$ Conjugate Vaccine, Infection and Immunity, 65:1710-1715 (1997).

Singh et al., "A Preliminary Evaluation of Alternative Adjuvants to Alum Using a Range of Established and New Generation Vaccine Antigens," Vaccine, 24:1680-1686 (2006).

Aluminum Adjuvants in Vaccines, http://www.immunizationinfo.org/issues/vaccine-components/aluminum-adjuvants-vaccines, Printed on Nov. 12, 2010.

* cited by examiner

FIGURE 1
FIGURE 1A
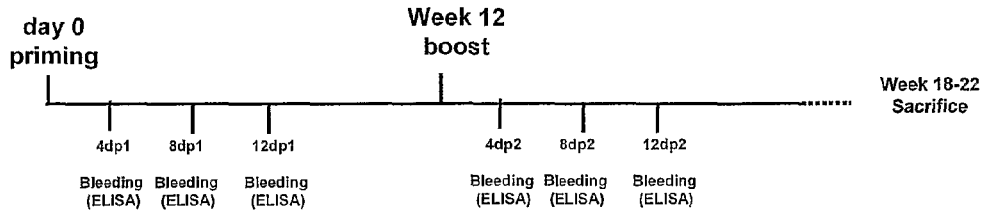
FIGURE 1B
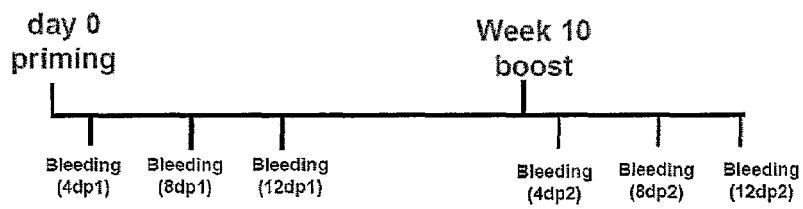
FIGURE 1C
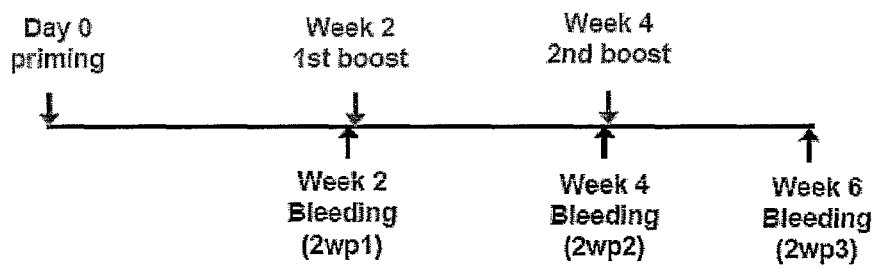
FIGURE 2
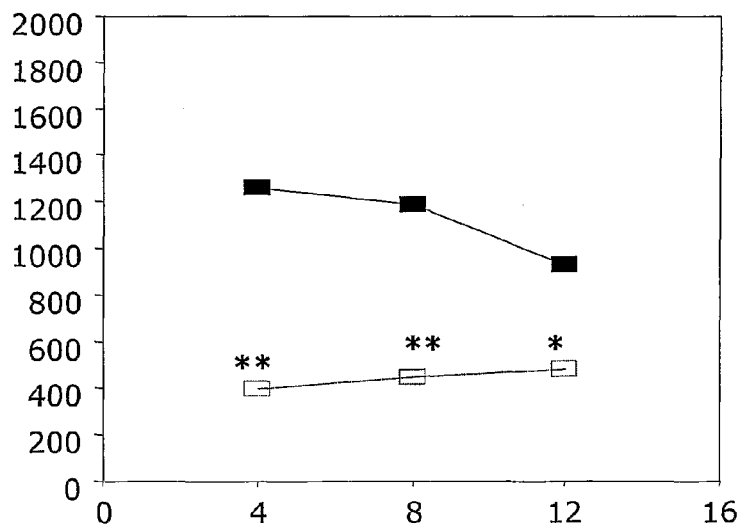

FIGURE 3
FIGURE 3A
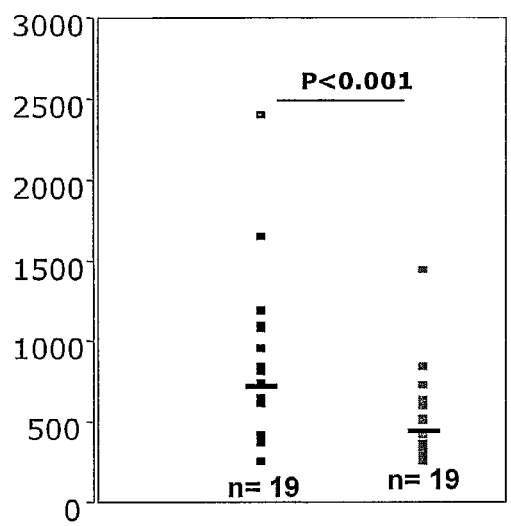
FIGURE 3B
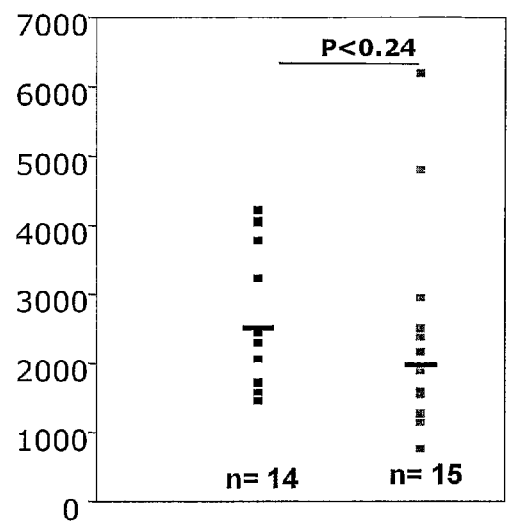
FIGURE 4
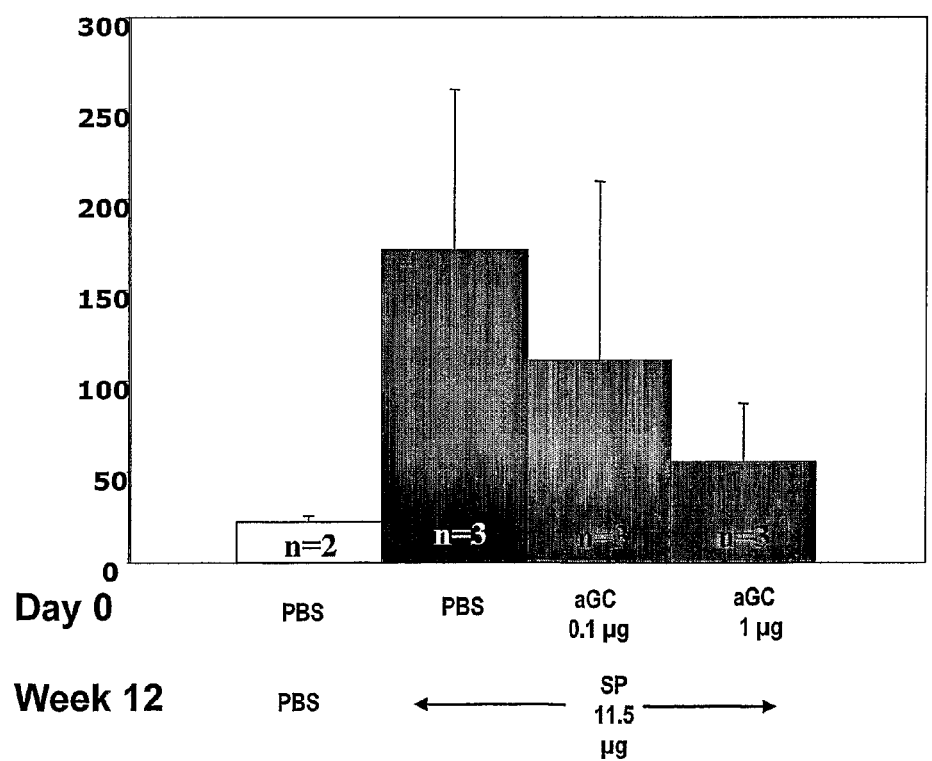

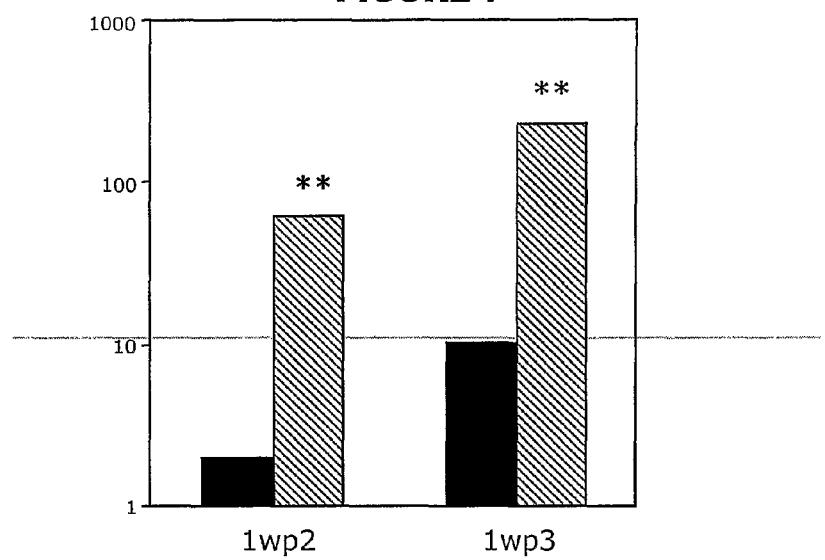
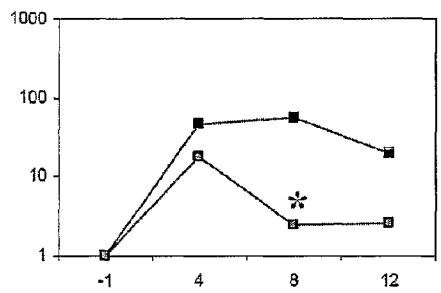
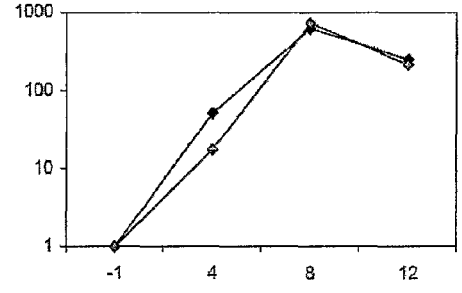
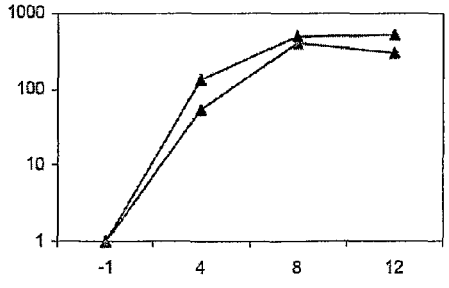
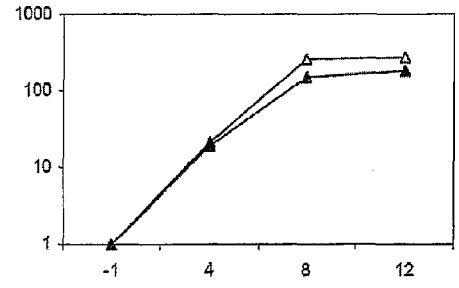

FIGURE 9
FIGURE 9A
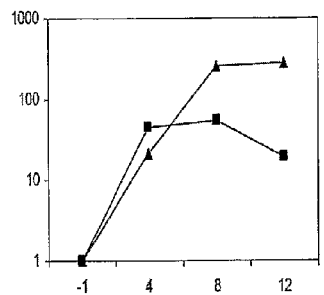
FIGURE 9B
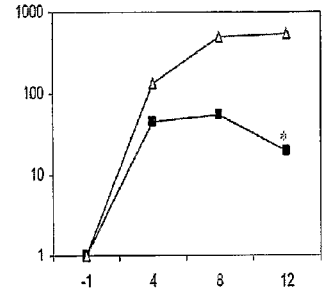
FIGURE 9C
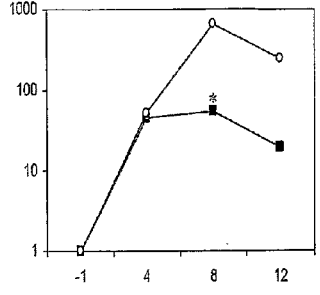
FIGURE 10
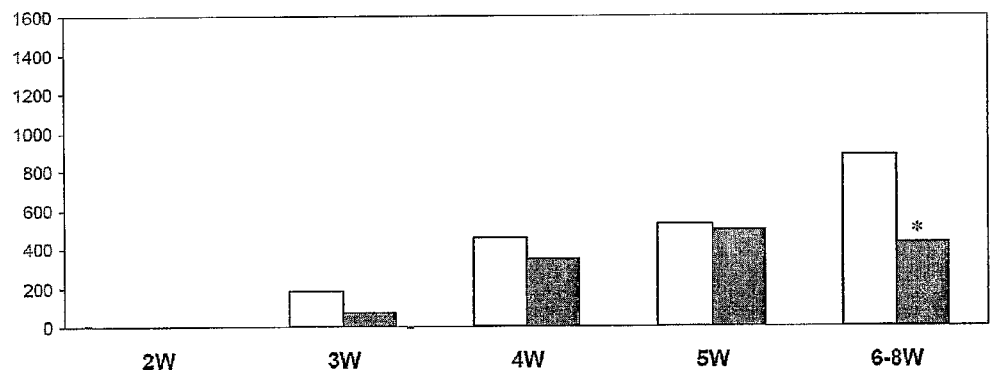
FIGURE 11
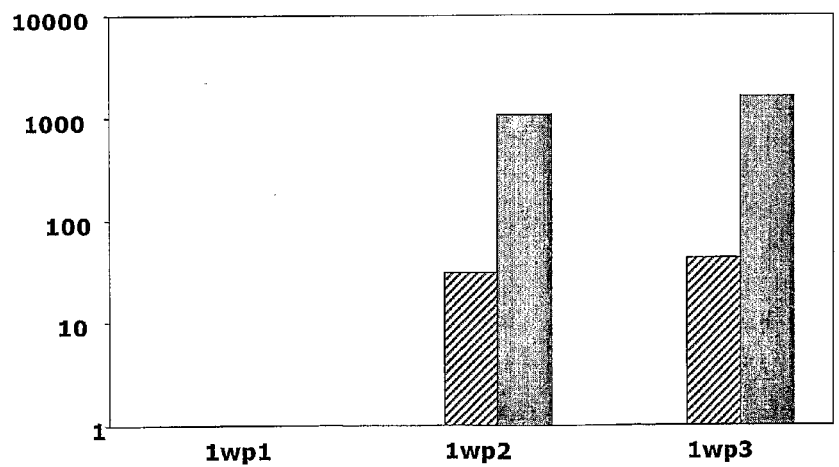

GLYCOSYLCERAMIDE ADJUVANT FOR SACCHARIDE ANTIGENS

All documents cited herein are incorporated by reference in their entirety.

TECHNICAL FIELD

This invention is in the field of vaccine adjuvants, particularly for saccharide antigens.

BACKGROUND ART

Vaccines often include adjuvants to boost immune activity. Examples of known adjuvants include aluminium salts, oil-in-water emulsions, saponins, cytokines, lipids and CpG oligonucleotides. Currently, only aluminium salts and the monophosphoryl lipid MF59™ are approved for human use. However, aluminium salts are subject to safety concerns and are incompatible with some antigens. There is therefore a need to develop further adjuvants.

α-galactosylceramide (α-GalCer) is a glycolipid, more specifically a glycosylceramide, originally isolated from marine sponges [1]. α-GalCer is presented by the MHC class I-like molecule, CD1d, to invariant Natural Killer T cells and was originally investigated for its ability to induce a Natural Killer T cell response against tumour cells [2]. Invariant Natural Killer T cells have been also shown to induce B cell activation, enhancing B cell proliferation and antibody production [3, 4]. Recently, α-GalCer has been shown to act as an adjuvant for a variety of co-administered protein antigens [5]. Coadministration of α-GalCer with irradiated sporozoites or recombinant viruses expressing a malaria antigen has been shown to enhance the level of protective anti-malaria immunity in mice [6]. α-GalCer has also been shown to act as an adjuvant for a DNA vaccine encoding HIV-1 gag and env genes [7].

However, not all vaccines contain protein antigens. Several commercially available vaccines contain saccharide antigens. For example, Pneumovax™ is a vaccine containing saccharide antigens from 23 pneumococcal serotypes. Mencevax™ and Menomune™ are meningococcal vaccines containing saccharide antigens from *Neisseria meningitidis* A, C, Y and W-135. It would therefore be desirable to extend the use of α-GalCer as an adjuvant to saccharide antigens.

Despite the success of α-GalCer as an adjuvant for DNA and protein antigens, the inventors have surprisingly found that it does not act as an adjuvant for some saccharide antigens. On the contrary, administration of α-GalCer with these antigens has been found to result in a substantial decrease in antibody titres relative to unadjuvanted controls. It is an object of the invention to overcome the problem of inhibition of anti-saccharide antibody responses when α-GalCer is present.

DISCLOSURE OF THE INVENTION

Surprisingly, it has been found that this suppression of the anti-saccharide immune response in the presence of α-GalCer can be reversed if the saccharide antigen is conjugated to a carrier, and that the immune response to the saccharide antigen can even be enhanced. The invention therefore provides a composition comprising: (a) a saccharide antigen conjugated to a carrier; and (b) an α-glycosylceramide adjuvant The α-glycosylceramide Adjuvants The adjuvant included in the compositions of the invention may be any suitable α-glycosylceramide known in the art. Preferably, the α-glycosylceramide adjuvant is a compound of formula (I):

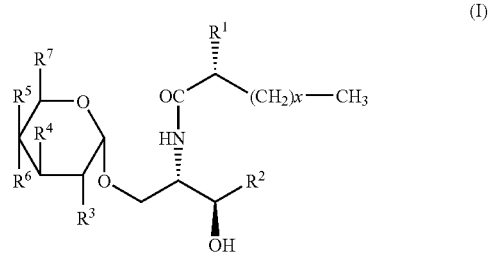

wherein
$R^1$ represents H or OH,
X represents an integer between 1 and 30,
$R^2$ represents a substituent selected from the group consisting of the following (a) to (e) (wherein Y represents an integer between 5 and 17);
(a) —$CH_2(CH_2)_YCH_3$
(b) —$CH(OH)(CH_2)_YCH_3$
(c) —$CH(OH)(CH_2)_YCH(CH_3)_2$
(d) —$CH=CH(CH_2)_YCH_3$
(e) —$CH(OH)(CH_2)_YCH(CH_3)CH_2CH_3$,
$R^3$ represents H, OH, $NH_2$, $NHCOCH_3$ or a monosaccharide,
$R^4$ represents OH or a monosaccharide,
$R^5$ represents H, OH or a monosaccharide,
$R^6$ represents H, OH or a monosaccharide, and
$R^7$ represents H, $CH_3$, $CH_2OH$ or a monosaccharide.

X is preferably between 7 and 27, more preferably between 9 and 24, and more preferably between 13 and 20. Y is preferably between 7 and 15, and more preferably between 9 and 13.

Where $R^3$ is a monosaccharide, it preferably selected from α-D-galactopyranose, β-D-galactopyranose, α-D-glucopyranose or β-D-glucopyranose.

Where $R^4$ is a monosaccharide, it is preferably selected from β-D-galactofuranose or N-acetyl α-D-galactopyranose.

Where $R^5$ is a monosaccharide, it is preferably selected from α-D-galactopyranose, β-D-galactopyranose, α-D-glucopyranose or β-D-glucopyranose.

Where $R^6$ is a monosaccharide, it is preferably selected from α-D-galactopyranose, β-D-galactopyranose, α-D-glucopyranose or β-D-glucopyranose.

Where $R^7$ is a monosaccharide, it is preferably selected from methyl α-Dgalactopyranoside, methyl β-D-galactopyranoside, methyl α-D-glucopyranoside or methyl β-D-glucopyranoside.

Preferably, $R^5$ and $R^6$ are different. Preferably, one of $R^5$ and $R^6$ is H.

Further examples of α-glycosylceramide adjuvants suitable for inclusion in the compositions of the invention are provided in reference 2.

Preferably, the α-glycosylceramide adjuvant is an α-galactosylceramide (α-GalCer) (i.e. $R^3$=OH, $R^4$=OH, $R^5$=OH, $R^6$=H and $R^7$=$CH_2OH$). α-GalCer included in the compositions of the invention may be isolated directly from marine sponges or may be a chemically synthesised product. Examples of α-galactosylceramides suitable for use in the compositions of the invention are provided in reference 8. A preferred α-galactosylceramide is KRN7000, which has the formula (2S,3S,4R)-1-O-(α-D-galactopyranosyl)-2-(N-hexacosanoylamino)-1,3,4-octadecanetriol. The synthesis of KRN7000 is described in reference 8.

The α-glycosylceramide adjuvant may also be a truncated analog of α-GalCer in which the fatty acly chain and/or the sphingosine chain are truncated compared to α-GalCer. Examples of truncated analogs of α-GalCer are provided in reference 9. A preferred truncated analog of α-GalCer is 'OCH' in which the fatty acyl chain has a truncation of two hydrocarbons and the sphingosine chain has a truncation of nine hydrocarbons compared to the preferred α-GalCer (i.e. $R^1$=H, X=21, $R^2$=CH(OH)(CH$_2$)$_4$CH$_3$, $R^3$=OH, $R^4$=OH, $R^5$=OH, $R^6$=H and $R^7$=CH$_2$OH). Further preferred truncated analogs of α-GalCer include analogs in which the fatty acyl chain has a truncation of two hydrocarbons and the sphingosine chain has a truncation of seven or three hydrocarbons compared to α-GalCer (i.e. $R^1$=H, X=21, $R^3$=OH, $R^4$=OH, $R^5$=OH, $R^6$=H, $R^7$=CH$_2$OH and $R^2$ is either CH(OH)(CH$_2$)$_6$CH$_3$ or CH(OH)(CH$_2$)$_{10}$CH$_3$).

Saccharide Antigens

Preferably, the saccharide antigen conjugated to a carrier included in the compositions of the invention is a bacterial saccharide and in particular a bacterial capsular saccharide.

Examples of bacterial capsular saccharides which may be included in the compositions of the invention include capsular saccharides from *Neisseria meningitidis* (serogroups A, B, C, W135 or Y), *Streptococcus pneumoniae* (serotypes 4, 6B, 9V, 14, 18C, 19F or 23F), *Streptococcus agalactiae* (types Ia, Ib, II, III, IV, V, VI, VII, or VIII), *Haemophilus influenzae* (typeable strains: a, b, c, d, e or f), *Pseudomonas aeruginosa*, *Staphylococcus aureus*, etc. Other saccharides which may be included in the compositions of the invention include glucans (e.g. fungal glucans, such as those in *Candida albicans*), and fungal capsular saccharides e.g. from the capsule of *Cryptococcus neoformans*.

The *N. meningitidis* serogroup A (MenA) capsule is a homopolymer of (α1→6)-linked N-acetyl-D-mannosamine-1-phosphate, with partial O-acetylation in the C3 and C4 positions. The *N. meningitidis* serogroup B (MenB) capsule is a homopolymer of (α2→8)-linked sialic acid. The *N. meningitidis* serogroup C (MenC) capsular saccharide is a homopolymer of (α2→9) linked sialic acid, with variable O-acetylation at positions 7 and/or 8. The *N. meningitidis* serogroup W135 saccharide is a polymer consisting of sialic acid-galactose disaccharide units [→4)-D-Neup5Ac(7/9OAc)-α-(2→6)-D-Gal-α-(1→]. It has variable O-acetylation at the 7 and 9 positions of the sialic acid [10]. The *N. meningitidis* serogroup Y saccharide is similar to the serogroup W135 saccharide, except that the disaccharide repeating unit includes glucose instead of galactose [→4)-D-Neup5Ac(7/9OAc)-α-(2→6)-D-Glc-α-(1→]. It also has variable O-acetylation at positions 7 and 9 of the sialic acid.

The *H. influenzae* type b capsular (Hib) saccharide is a polymer of ribose, ribitol and phosphate ['PRP', (poly-3-β-D-ribose-(1,1)-D-ribitol-5-phosphate)].

The compositions of the invention may contain mixtures of saccharide antigen conjugates. Preferably, compositions of the invention comprise saccharide antigens from more than one serogroup of *N. meningitidis*, e.g. compositions may comprise saccharides conjugates from serogroups A+C, A+W135, A+Y, C+W135, C+Y, W135+Y, A+C+W135, A+C+Y, C+W135+Y, A+C+W135+Y, etc. Preferred compositions comprise saccharide conjugates from serogroups C and Y. Other preferred compositions comprise saccharide conjugates from serogroups C, W135 and Y.

Where a mixture comprises meningococcal saccharides from serogroup A and at least one other serogroup saccharide, the ratio (w/w) of MenA saccharide to any other serogroup saccharide may be greater than 1 (e.g. 2:1, 3:1, 4:1, 5:1, 10:1 or higher). Preferred ratios (w/w) for saccharides from serogroups A:C:W135:Y are: 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1.

Further preferred compositions of the invention comprise a Hib saccharide conjugate and a saccharide conjugate from at least one serogroup of *N. meningitidis*, preferably from more than one serogroup of *N. meningitidis*. For example, a composition of the invention may comprise a Hib conjugate and cojugates from *N. meningitidis* serogroups A, C, W135 and Y.

The invention further includes compositions comprising *Streptococcus pneumoniae* saccharide conjugates. Preferably, the compositions comprise saccharide conjugates from more than one serotype of *Streptococcus pneumoniae*. Preferred compositions comprise saccharide conjugates from *Streptococcus pneumoniae* serotypes 4, 6B, 9V, 14, 18C, 19F and 23F (7-valent). Compositions may further comprise saccharide conjugates from *Streptococcus pneumoniae* serotypes 4, 6B, 9V, 14, 18C, 19F 23F, 1 and 5 (9-valent) or may comprise saccharide conjugates from *Streptococcus pneumoniae* serotypes 4, 6B, 9V, 14, 18C, 19F, 23F, 1, 5, 3 and 7F (11-valent).

Further preferred compositions of the invention comprise pneumococcal saccharide conjugates and saccharide conjugates from Hib and/or *N. meningitidis*. Preferably, compositions of the invention may comprise saccharide conjugates from *S. pneumoniae* serotypes 4, 6B, 9V, 14, 18C, 19F and 23F and a Hib saccharide conjugate. Preferably, compositions of the invention may comprise saccharide conjugates from *S. pneumoniae* serotypes 4, 6B, 9V, 14, 18C, 19F and 23F and saccharide conjugates from *N. meningitidis* serogroups A, C, W135 and Y. Compositions according to the invention may also comprise saccharide conjugates from *S. pneumoniae* serotypes 4, 6B, 9V, 14, 18C, 19F and 23F, a Hib saccharide conjugate and saccharide conjugates from *N. meningitidis* serogroups A, C, W135 and Y.

It is preferred that the protective efficacy of individual saccharide antigen conjugates is not removed by combining them, although actual immunogenicity (e.g. ELISA titres) may be reduced.

Preparation of Capsular Saccharide Antigens

Methods for the preparation of capsular saccharide antigens are well known. For example, ref. 11 describes the preparation of saccharide antigens from *N. meningitidis*. The preparation of saccharide antigens from *H. influenzae* is described in chapter 14 of ref. 12). The preparation of saccharide antigens and conjugates from *S. pneumoniae* is described in the art. For example, Prevenar™ is a 7-valent pneumococcal conjugate vaccine. Processes for the preparation of saccharide antigens from *S. agalactiae* is described in detail in refs. 13 and 14.

The saccharide antigens may be chemically modified. For instance, they may be modified to replace one or more hydroxyl groups with blocking groups. This is particularly useful for meningococcal serogroup A where the acetyl groups may be replaced with blocking groups to prevent hydrolysis [15]. Such modified saccharides are still serogroup A saccharides within the meaning of the present invention.

Capsular saccharides may be used in the form of oligosaccharides. These are conveniently formed by fragmentation of purified capsular polysaccharide (e.g. by hydrolysis), which will usually be followed by purification of the fragments of the desired size.

Fragmentation of polysaccharides is preferably performed to give a final average degree of polymerisation (DP) in the oligosaccharide of less than 30. DP can conveniently be measured by ion exchange chromatography or by colorimetric assays [16].

If hydrolysis is performed, the hydrolysate will generally be sized in order to remove short-length oligosaccharides [17]. This can be achieved in various ways, such as ultrafiltration followed by ion-exchange chromatography. Oligosaccharides with a degree of polymerisation of less than or equal to about 6 are preferably removed for serogroup A, and those less than around 4 are preferably removed for serogroups W135 and Y.

Carriers

Preferably, the carrier is a protein. Preferred carrier proteins to which the saccharide antigens are conjugated in the compositions of the invention are bacterial toxins, such as diphtheria toxoid or tetanus toxoid. Suitable carrier proteins include the CRM197 mutant of diphtheria toxin [18-20], diphtheria toxoid, the *N. meningitidis* outer membrane protein [21], synthetic peptides [22,23], heat shock proteins [24, 25], pertussis proteins [26,27], cytokines [28], lymphokines [28], hormones [28], growth factors [28], artificial proteins comprising multiple human CD4+ T cell epitopes from various pathogen-derived antigens [29] such as the N19 protein [30], protein D from *H. influenzae* [31,32], pneumococcal surface protein PspA [33], pneumolysin [34], iron-uptake proteins [35], toxin A or B from *C. difficile* [36], etc.

Attachment of the saccharide antigen to the carrier is preferably via a —NH$_2$ group e.g. in the side chain of a lysine residue in a carrier protein, or of an arginine residue. Where a saccharide has a free aldehyde group then this can react with an amine in the carrier to form a conjugate by reductive amination. Attachment may also be via a —SH group e.g. in the side chain of a cysteine residue.

Where the composition contain more than one saccharide antigen, it is possible to use more than one carrier e.g. to reduce the risk of carrier suppression. Thus different carriers can be used for different saccharide antigens. e.g. *Neisseria meningitidis* serotype A saccharides might be conjugated to CRM197 while type C saccharides might be conjugated to tetanus toxoid. It is also possible to use more than one carrier for a particular saccharide antigen. The saccharides might be in two groups, with some conjugated to CRM197 and others conjugated to tetanus toxoid. In general, however, it is preferred to use the same carrier for all saccharides.

A single carrier protein might carry more than one saccharide antigen [37,38]. For example, a single carrier protein might have conjugated to it saccharides from different pathogens or from different serotypes of the same pathogen. To achieve this goal, different saccharides can be mixed prior to the conjugation reaction. In general, however, it is preferred to have separate conjugates for each serogroup, with the different saccharides being mixed after conjugation. The separate conjugates may be based on the same carrier.

Conjugates with a saccharide:protein ratio (w/w) of between 1:5 (i.e. excess protein) and 5:1 (i.e. excess saccharide) are preferred. Ratios between 1:2 and 5:1 are preferred, as are ratios between 1:1.25 and 1:2.5.

Conjugates may be used in conjunction with free carrier [39]. When a given carrier protein is present in both free and conjugated form in a composition of the invention, the unconjugated form is preferably no more than 5% of the total amount of the carrier protein in the composition as a whole, and more preferably present at less than 2% by weight.

After conjugation, free and conjugated saccharides can be separated. There are many suitable methods, including hydrophobic chromatography, tangential ultrafiltration, diafiltration etc. [see also refs. 40 & 41, etc.].

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [42, 43, etc.]). Other suitable techniques use carbodiimides, hydrazides, active esters, norborane, p-nitrobenzoic acid, N-hydroxysuccinimide, S-NHS, EDC, TSTU (see also the introduction to reference 44).

Linkages via a linker group may be made using any known procedure, for example, the procedures described in references 45 and 46. One type of linkage involves reductive amination of the polysaccharide, coupling the resulting amino group with one end of an adipic acid linker group, and then coupling a protein to the other end of the adipic acid linker group [47, 48]. Other linkers include B-propionamido [49], nitrophenyl-ethylamine [50], haloacyl halides [51], glycosidic linkages [52], 6-aminocaproic acid [53], ADH [54], C4 to C12 moieties [55] etc. As an alternative to using a linker, direct linkage can be used. Direct linkages to the protein may comprise oxidation of the polysaccharide followed by reductive amination with the protein, as described in, for example, references 56 and 57.

A process involving the introduction of amino groups into the saccharide (e.g. by replacing terminal =O groups with —NH2) followed by derivatisation with an adipic diester (e.g. adipic acid N-hydroxysuccinimido diester) and reaction with carrier protein is preferred.

After conjugation, free and conjugated saccharides can be separated. There are many suitable methods, including hydrophobic chromatography, tangential ultrafiltration, diafiltration etc. [see also refs. 58 & 59, etc.].

Where the composition of the invention includes a depolymerised saccharide, it is preferred that depolymerisation precedes conjugation.

Further Antigenic Components of the Compositions

The compositions of the invention include at least one saccharide antigen conjugated to a carrier. However, the composition of the invention may include one or more of the following antigens, in addition to the saccharide antigen(s) conjugated to carrier(s) described above:

a protein antigen from *N. meningitidis* serogroup B, such as those in refs. 60 to 66, with protein '287' (see below) and derivatives (e.g. 'ΔG287') being particularly preferred.

an outer-membrane vesicle (OMV) preparation from *N. meningitidis* serogroup B, such as those disclosed in refs. 67, 68, 69, 70 etc.

a protein antigen from *S. pneumoniae* (e.g. from PhtA, PhtD, PhtB, PhtE, SpsA, LytB, LytC, LytA, Sp125, Sp101, Sp128, Sp130 and Sp133, as disclosed in reference 71.)

an antigen from hepatitis A virus, such as inactivated virus [e.g. 72, 73; chapter 15 of ref. 78].

an antigen from hepatitis B virus, such as the surface and/or core antigens [e.g. 73,74; chapter 16 of ref. 78].

an antigen from hepatitis C virus [e.g. 75].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 76 & 77; chapter 21 of ref. 78].

a diphtheria antigen, such as a diphtheria toxoid [e.g. chapter 13 of ref. 78].

a tetanus antigen, such as a tetanus toxoid [e.g. chapter 27 of ref. 78].

an antigen from *N. gonorrhoeae* [e.g. 60, 61, 62].

an antigen from *Chlamydia pneumoniae* [e.g. 79, 80, 81, 82, 83, 84, 85].

an antigen from *Chlamydia trachomatis* [e.g. 86].

an antigen from *Porphyromonas gingivalis* [e.g. 87].

polio antigen(s) [e.g. 88, 89; chapter 24 of ref. 78] such as IPV.

rabies antigen(s) [e.g. 90] such as lyophilised inactivated virus [e.g. 91, RabAvert™].

measles, mumps and/or rubella antigens [e.g. chapters 19, 20 and 26 of ref. 78].

antigens from *Helicobacter pylori* such as CagA [92 to 95], VacA [96, 97], NAP [98, 99, 100], HopX [e.g. 101], HopY [e.g. 101] and/or urease.

influenza antigen(s) [e.g. chapters 17 & 18 of ref. 78], such as the haemagglutinin and/or neuraminidase surface proteins.

an antigen from *Moraxella catarrhalis* [e.g. 102].

a protein antigen from *Streptococcus agalactiae* (group B streptococcus) [e.g. 103, 104].

an antigen from *Streptococcus pyogenes* (group A *streptococcus*) [e.g. 104, 105, 106].

an antigen from *Staphylococcus aureus* [e.g. 107].

antigen(s) from a paramyxovirus such as respiratory syncytial virus (RSV [108, 109]) and/or parainfluenza virus (PIV3 [110]).

an antigen from *Bacillus anthracis* [e.g. 111, 112, 113].

an antigen from a virus in the flaviviridae family (genus flavivirus), such as from yellow fever virus, Japanese encephalitis virus, four serotypes of Dengue viruses, tick-borne encephalitis virus, West Nile virus.

a pestivirus antigen, such as from classical porcine fever virus, bovine viral diarrhoea virus, and/or border disease virus.

a parvovirus antigen e.g. from parvovirus B19.

The mixture may comprise one or more of these further antigens, which may be detoxified where necessary (e.g. detoxification of pertussis toxin by chemical and/or genetic means).

Where a diphtheria antigen is included in the mixture it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens in the mixture will typically be present at a concentration of at least 1 µg/ml each. In general, the concentration of any given antigen will be sufficient to elicit an immune response against that antigen.

As an alternative to using proteins antigens in the mixture, nucleic acid encoding the antigen may be used. Protein components of the mixture may thus be replaced by nucleic acid (preferably DNA e.g. in the form of a plasmid) that encodes the protein. Similarly, compositions of the invention may comprise proteins which mimic saccharide antigens e.g. mimotopes [114] or anti-idiotype antibodies.

Formulation of Pharmaceutical Compositions

The conjugates and α-glycosylceramide adjuvant of the invention are particularly suited to inclusion in immunogenic compositions and vaccines. A process of the invention may therefore include the step of formulating the conjugate and α-glycosylceramide adjuvant as an immunogenic composition or vaccine. The invention provides a composition or vaccine obtainable in this way.

Immunogenic compositions and vaccines of the invention will, in addition to saccharide antigen(s) conjugated to carrier protein(s) and α-glycosylceramide adjuvant, typically comprise 'pharmaceutically acceptable carriers', which include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, trehalose [115], lipid aggregates (such as oil droplets or liposomes), and inactive virus particles. Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. A thorough discussion of pharmaceutically acceptable excipients is available in ref. 116.

Immunogenic compositions used as vaccines comprise an immunologically effective amount of saccharide antigen, as well as any other of the above-mentioned components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses).

The vaccine may be administered in conjunction with other immunoregulatory agents. The α-glycosylceramide acts as an adjuvant within the immunogenic compositions of the invention. The vaccine may include additional adjuvants. Such adjuvants include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 117], or mixtures of different mineral compounds, with the compounds taking any suitable form (e.g. gel, crystalline, amorphous, etc.), and with adsorption being preferred. The mineral containing compositions may also be formulated as a particle of metal salt [118].

A typical aluminium phosphate adjuvant is amorphous aluminium hydroxyphosphate with $PO_4/Al$ molar ratio between 0.84 and 0.92, included at 0.6 mg $Al^{3+}$/ml. Adsorption with a low dose of aluminium phosphate may be used e.g. between 50 and 100 µg $Al^{3+}$ per conjugate per dose. Where an aluminium phosphate it used and it is desired not to adsorb an antigen to the adjuvant, this is favoured by including free phosphate ions in solution (e.g. by the use of a phosphate buffer).

B. Oil Emulsions

Oil emulsion compositions suitable for use as adjuvants in the invention include squalene-water emulsions, such as MF59 [Chapter 10 of ref. 117; see also ref. 119] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

C. Saponin Formulations [Chapter 22 of Ref. 117]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 120. Saponin formulations may also comprise a sterol, such as cholesterol [121].

Combinations of saponins and cholesterols can be used to form unique particles called immunostimulating complexes (ISCOMs) [chapter 23 of ref. 117]. ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in refs. 121-123. Optionally, the ISCOMS may be devoid of additional detergent [124].

A review of the development of saponin based adjuvants can be found in refs. 125 & 126.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 127-132. Virosomes are discussed further in, for example, ref. 133

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 134. Such "small particles" of 3dMPL are small enough to be sterile filtered through a 0.2 μm membrane [134]. Other non-toxic LPS derivatives include monophosphoryl lipid A mimics, such as aminoalkyl glucosaminide phosphate derivatives e.g. RC-529 [135,136].

Lipid A derivatives include derivatives of lipid A from *Escherichia coli* such as OM-174. OM-174 is described for example in refs. 137 & 138.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 139, 140 and 141 disclose possible analog substitutions e.g. replacement of guanosine with 2'-deoxy-7-deazaguanosine. The adjuvant effect of CpG oligonucleotides is further discussed in refs. 142-147.

The CpG sequence may be directed to TLR9, such as the motif GTCGTT or TTCGTT [148]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 149-151. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 148 & 152-154.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 155 and as parenteral adjuvants in ref. 156. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 157-164. Numerical reference for amino acid substitutions is preferably based on the alignments of the A and B subunits of ADP-ribosylating toxins set forth in ref. 165, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [166], etc.) [167], interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [168] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [169].

H. Microparticles

Microparticles may also be used as adjuvants in the invention. Microparticles (i.e. a particle of ~100 nm to 150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref. 117)

Examples of liposome formulations suitable for use as adjuvants are described in refs. 170-172.

J. Polyoxyethylene Ether and Polyoxyethylene Ester Formulations

Adjuvants suitable for use in the invention include polyoxyethylene ethers and polyoxyethylene esters [173]. Such formulations further include polyoxyethylene sorbitan ester surfactants in combination with an octoxynol [174] as well as polyoxyethylene alkyl ethers or ester surfactants in combination with at least one additional non-ionic surfactant such as an octoxynol [175]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 176 and 177.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 178 and 179.

The invention may also comprise combinations of aspects of one or more of the adjuvants identified above. For example, the following adjuvant compositions may be used in the invention: (1) a saponin and an oil-in-water emulsion [180]; (2) a saponin (e.g. QS21)+a non-toxic LPS derivative (e.g. 3dMPL) [181]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [182]; (5) combinations of 3dMPL with, for example, QS21 and/or oil-in-water emulsions [183]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 117.

Medical Methods and Uses

Once formulated, the compositions of the invention can be administered directly to the subject. The subjects to be treated can be animals; in particular, human subjects can be treated. The vaccines are particularly useful for vaccinating children and teenagers. They may be delivered by systemic and/or mucosal routes.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect. Direct delivery of the compositions will generally be parenteral (e.g. by injection, either subcutaneously, intraperitoneally, intravenously or intramuscularly or delivered to the interstitial space of a tissue). The compositions can also be administered into a lesion. Other modes of administration include oral and pulmonary administration, suppositories, and transdermal or transcutaneous applications (e.g. see ref. 184), needles, and hyposprays. Dosage treatment may be a single dose schedule or a multiple dose schedule (e.g. including booster doses).

Vaccines of the invention are preferably sterile. They are preferably pyrogen-free. They are preferably buffered e.g. at between pH 6 and pH 8, generally around pH 7. Where a vaccine comprises an aluminium hydroxide salt, it is preferred to use a histidine buffer [185].

Vaccines of the invention may comprise detergent (e.g. a Tween, such as Tween 80) at low levels (e.g. <0.01%). Vaccines of the invention may comprise a sugar alcohol (e.g. mannitol) or trehalose e.g. at around 15 mg/ml, particularly if they are to be lyophilised.

Optimum doses of individual antigens can be assessed empirically. In general, however, saccharide antigens of the invention will be administered at a dose of between 0.1 and 100 μg of each saccharide per dose, with a typical dosage volume of 0.5 ml. The dose is typically between 5 and 20 μg per saccharide per dose. These values are measured as saccharide.

Vaccines according to the invention may either be prophylactic (i.e. to prevent infection) or therapeutic (i.e. to treat disease after infection), but will typically be prophylactic.

The invention provides a saccharide antigen conjugated to a carrier protein and an α-glycosylceramide adjuvant for use in medicine.

The invention also provides a method of raising an immune response in a patient, comprising administering to a patient a vaccine according to the invention. In particular, the invention provides a method of raising an immune response in a patient, comprising administering to a patient a saccharide antigen conjugated to a carrier and an α-glycosylceramide adjuvant. The immune response is preferably protective against meningococcal disease, pneumococcal disease or *H. influenzae* and may comprise a humoral immune response and/or a cellular immune response. The patient may be an adult or a child. The patient may be aged 0-6 months, 6-12 months, 1-5 years, 5-15 years, 15-55 years or greater than 55 years. Preferably, the patient is a child. The method may raise a booster response, in a patient that has already been primed against meningococcus, pneumococcus or *H. influenzae*.

The saccharide antigen conjugate and α-glycosylceramide adjuvant may be administered simultaneously, sequentially or separately. For example, the α-glycosylceramide adjuvant may be administered to prime the mammal before administration of the saccharide antigen conjugate or after the administration of the saccharide antigen conjugate to boost the mammal's immune response to that conjugate. Where more than one saccharide antigen conjugate is being administered, the saccharide antigen conjugates may be administered simultaneously with the α-glycosylceramide adjuvant being administered separately, simultaneously or sequentially to the mixture of saccharide antigen conjugates.

The method of raising an immune response may comprise administering a first dose of a saccharide antigen conjugated to a carrier and an α-glycosylceramide adjuvant, and subsequently administering an optional second unadjuvanted dose of the saccharide antigen conjugated to the carrier. The first dose of the saccharide antigen conjugate and α-glycosylceramide adjuvant may be administered simultaneously, sequentially or separately.

The invention also provide the use of a saccharide antigen conjugated to a carrier in the manufacture of a medicament for raising an immune response in a patient, wherein the medicament is administered with an α-glycosylceramide adjuvant.

The invention also provides the use of an α-glycosylceramide adjuvant in the manufacture of a medicament for raising an immune response in a patient, wherein the medicament is administered with a saccharide antigen conjugated to a carrier.

The invention also provides the use of a saccharide antigen conjugated to a carrier and an α-glycosylceramide adjuvant in the manufacture of a medicament for raising an immune response in a patient.

The invention also provides the use of a saccharide antigen conjugated to a carrier in the manufacture of a medicament for raising an immune response in a patient, where the patient has been pre-treated with an α-glycosylceramide adjuvant.

The invention further provides the use of a α-glycosylceramide adjuvant in the manufacture of a medicament for raising an immune response in a patient, where the patient has been pre-treated with a saccharide conjugated to a carrier.

The invention also provides the use of a saccharide antigen conjugated to a carrier in the manufacture of a medicament for raising an immune response in a patient, wherein said patient has been pre-treated with a saccharide antigen conjugated to a carrier and an α-glycosylceramide adjuvant.

The medicament is preferably an immunogenic composition (e.g. a vaccine). The medicament is preferably for the prevention and/or treatment of a disease caused by a *Neisseria* (e.g. meningitis, septicaemia, gonorrhoea etc.), by *H. influenzae* (e.g. otitis media, bronchitis, pneumonia, cellulitis, pericarditis, meningitis etc.) or by pneumococcus (e.g. meningitis, sepsis, pneumonia, etc). The prevention and/or treatment of bacterial meningitis is thus preferred.

Vaccines can be tested in standard animal models (e.g. see ref. 186).

The invention further provides a kit comprising: a) a saccharide antigen conjugated to a carrier and b) an α-glycosylceramide adjuvant.

DEFINITIONS

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

BRIEF DESCRIPTION OF THE DRAWINGS

FIG. 1:

Figure 5:
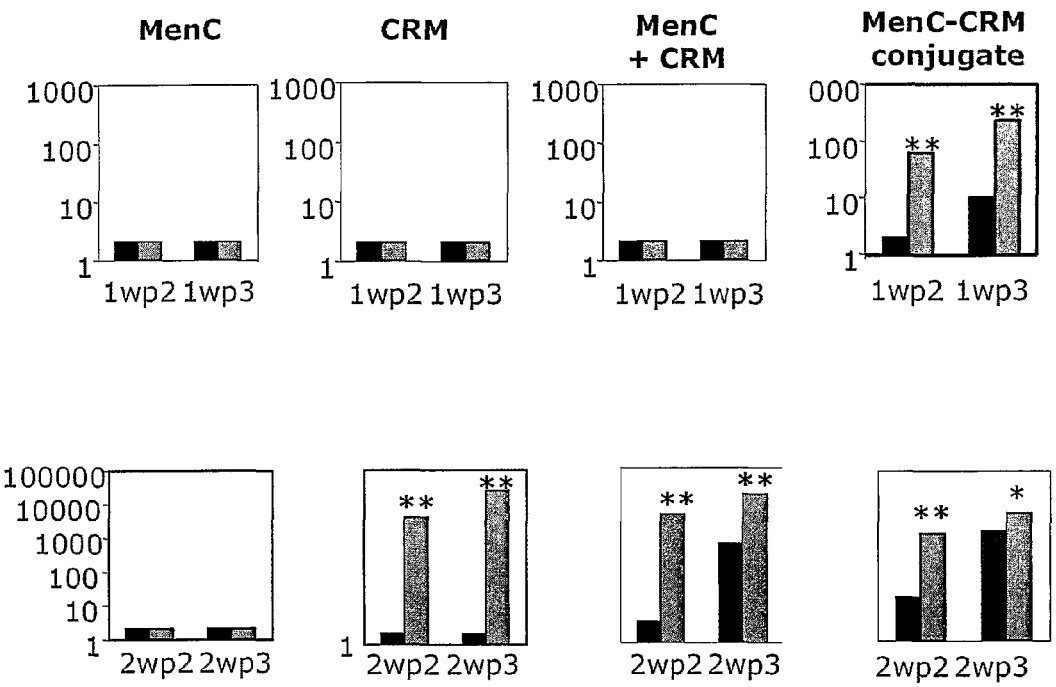

A) Immunisation schedule for mice with *S. pneumoniae* polysaccharides with or without α-GalCer. Four groups of six-week old female mice (C57L/6 WT, CD1d+/−, CD1d−/− or JA18−/− were immunised with: 1) PBS, 2) 0.1 μg of α-GalCer, 3) 3.5 μg-10 μg of a mixture of polysaccharides derived from 23 different serotypes of *S. pneumoniae* (Streptopur), or 4) 3.5 μg-10 μg of Streptopur (SP) and 0.1 μg of α-GalCer. Immunisation was intramuscular in a volume of 50 μl. The mice were bled 4, 8, and 12 days after priming (4dp1, 8dp1, 12dp1) and the level of antibodies against *S. pneumoniae* in the blood was determined by ELISA. Ten or twelve weeks after priming, all the mice were immunised with a booster dose of 3.5 μg-10 μg SP alone. The mice were bled 4, 8, and 12 days after boosting (4dp2, 8dp2, 12dp2) and the level of antibodies against *S. pneumoniae* in the blood was determined by ELISA. 18 to 22 weeks after priming, the mice were sacrificed and the number of *S. pneumoniae*-specific B cells was determined by Elispot.

B) Immunisation schedule for mice with *S. pneumoniae* polysaccharides with or without α-GalCer. As for FIG. 1A, but immunisations used 3.5 μg of SP in 50 μl.

C) Immunisation schedule for mice with different polysaccharides, plain, conjugated or admixed with protein carriers, with and without α-GalCer. Ten groups of wild-type C57BL/6 mice were primed on day 0 with: 1) PBS, 2) 0.1 μg with α-GalCer, 3) 10 μg MenC polysaccharide, 4) 20 μg CRM protein carrier, 5) 30 μg of a MenC-CRM conjugate, 6) 10 μg MenC polysaccharide admixed with CRM protein carrier, or the compositions in 3)-6) and α-GalCer (groups 7-10). Mice were boosted two and four weeks after they were primed with the same composition with which they were primed. Mice were bled 2, 4 and 6 weeks after initial priming (2wp1, 2wp2 and 2wp3) and the levels of antibodies against both the MenC polysaccharide and the CRM carrier were measured.

FIG. 2: *S. pneumoniae*-specific antibody titers are lower in mice primed with Streptopur and α-GalCer compared with mice primed with Streptopur alone. The *S. pneumoniae*-specific IgM titre (geomean) in mice 4, 8 and 12 days after priming with 3.5 μg of Streptopur (SP) alone (black boxes) or with 3.5 μg of Streptopur and 0.1 μg of α-GalCer (clear boxes) is shown. (* denotes p<0.05 vs SP alone, ** denotes p<0.01 vs SP alone).

FIG. 3: *S. pneumoniae*-specific antibody titers are lower in mice primed with Streptopur and α-GalCer and boosted with Streptopur compared with mice primed and boosted with Streptopur alone. A) The variation in *S. pneumoniae*-specific IgM titre (geomean) in mice 8 days after priming with 3.5-11.5 μg of Streptopur and PBS (black) or 8 days after priming with 3.5-11.5 μg of Streptopur and 0.1 μg of α-GalCer (grey). (These data are pooled from four experiments). B) The variation in *S. pneumoniae*-specific IgM titre (geomean) of the same mice 8 days after boosting with 3.5-11.5 μg of Streptopur. (These data are pooled from experiments 18, 19 and 29 conducted.) Results for mice primed with 3.5-11.5 μg of Streptopur are shown in black and results for mice primed with 3.5 μg of Streptopur and 0.1 μg of α-GalCer are shown in grey.

FIG. 4: Number of *S. pneumoniae*-specific B cells per $10^6$ splenocytes is lower in mice primed with α-GalCer and boosted with Streptopur compared with mice primed with PBS and boosted with Streptopur. Two groups of mice were primed on day 0 with 0.1 μg or 1.0 μg of α-GalCer (aGC) and immunised with 11.5 μg of Streptopur (SP) 12 weeks later. A third group of mice was immunised with PBS on day 0 and 11.5 µg of SP 12 weeks later. A fourth group of mice was immunised with PBS on both day 0 and 12 weeks later. Twenty-two weeks after initial priming, the mice were sacrificed and the number of S. pneumoniae-specific B cells per $10^6$ splenocytes was determined by Elispot.

FIG. 5: α-GalCer enhances the specific antibody response against both the MenC polysaccharide and the CRM protein carrier in a MenC-CRM conjugate. Wild-type mice were primed with 10 µg MenC polysaccharide, 20 µg CRM protein carrier, 10 µg MenC polysaccharide admixed with CRM protein carrier (MenC+CRM), or 30 µg of a MenC-CRM conjugate, or the same compositions with α-GalCer. Mice were boosted two and four weeks after they were primed with the same composition with which they were primed. The top line of Figures shows the MenC-specific Ig titre in mice immunised with MenC, CRM, MenC+CRM or MenC-CRM conjugate alone (black) or MenC, CRM, MenC+CRM or MenC-CRM conjugate and α-GalCer (grey) one week post the second immunisation (1wp2) and one week post the second immunisation (2wp2). The second line of Figures shows the CRM-specific Ig titre in mice immunised with MenC, CRM, MenC+CRM or MenC-CRM conjugate alone (black) or MenC, CRM, MenC+CRM or MenC-CRM conjugate and α-GalCer (grey) two weeks post the second immunisation (2wp2) and two weeks post the third immunisation (2wp3).

Figure 6:
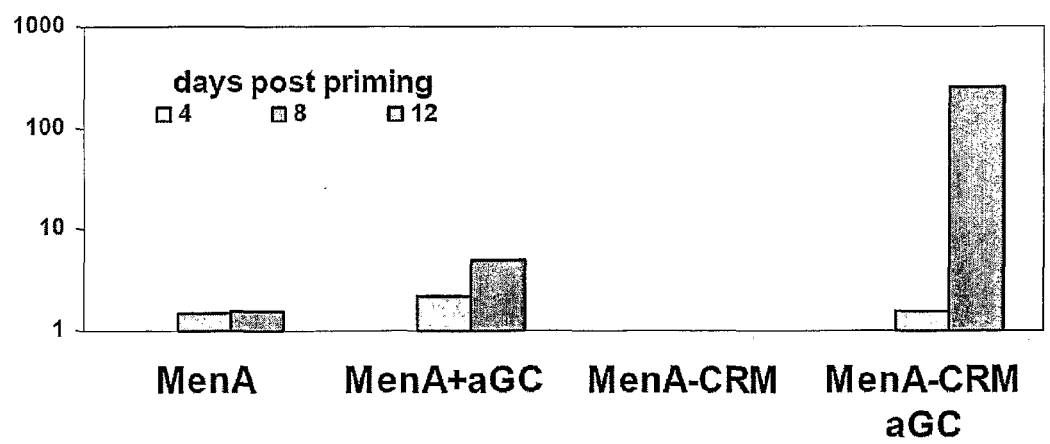

FIG. 6: α-GalCer enhances the immune response to a MenA-CRM conjugate. Mice were immunised with 10 µg MenA polysaccharide or MenA-CRM conjugate with or without α-GalCer. Antibodies titres against the MenA polysaccharide were measured 4, 8 and 12 days post priming. α-GalCer enhanced the immune response to the MenA polysaccharide.

FIG. 7: Antibody response is enhanced in mice immunised with α-GalCer and MenC-CRM conjugate. Mice were immunised with 30 µg of a MenC-CRM conjugate mixed with PBS (black) or α-GalCer. Each group of mice was immunised three times. The MenC-specific titre was measured one week post the second immunisation (1wp2) and one week post third immunisation (1wp3).

FIG. 8: α-GalCer-induced inhibition of the response to S. pneumoniae polysaccharides requires invariant NKT cells. The levels of S. pneumoniae-specific antibodies 4, 8 and 12 days after priming mice with 3.5 µg SP alone (grey symbols) or 3.5 µg SP and 0.1 µg of α-GalCer (black symbols) were compared in: A) wild-type mice, B) Ja18-/- mice, C) mCD1d-/- mice, and D) mCD1d-/+ mice. No significant difference was seen in antibody titres in Ja18-/-, CD1d-/- and CD1d-/+ mice immunised with Streptopur alone compared to Ja18-/-, CD1d-/- and CD1d-/+ mice immunised with Streptopur in combination with α-GalCer.

FIG. 9: Invariant NKT cells have a negative regulatory role on antibody responses to S. pneumoniae polysaccharides. The levels of S. pneumoniae-specific antibodies (IgM titer geomean) 4, 8 and 12 days after priming mice solely with Streptopur according to the protocol in FIG. 1B were compared. FIG. 9A compares antibody titres in C57 wild-type mice (squares) with antibody titres in C57 mCD1d+/- mice (triangles). FIG. 9B compares antibody titres in C57 wild-type mice (squares) with antibody titres in C57 mCD1d-/- mice (triangles). FIG. 9C compares antibody titres in C57 wild-type mice (squares) with antibody titres in C57 Ja281-/- mice (circles). Antibodies titers in wild-type mice were lower than in Ja18-/-, CD1-/- and CD1+/- mice.

FIG. 10: α-GalCer suppresses immune response to Streptopur in 3-8 week-old mice. The levels of S. pneumoniae specific IgM antibodies (geomean) were compared 8 days after priming mice aged 2 weeks (2W), 3 weeks (3W), 4 weeks (4W), 5 weeks (5W) and 6-8 weeks (6-8W) with 3.5 µg of Streptopur (SP) alone (clear) or with 3.5 µg of Streptopur and 0.1 µg of α-GalCer (black).

FIG. 11: Antibody response is enhanced in mice immunised with α-GalCer and Hib-HSA conjugate. Mice were immunised with 15 µg of a Hib-Human Serum Albumin (Hib-HSA) conjugate mixed with PBS (results too low to be detected), α-GalCer (hatched) or MF59 (grey). Each group of mice was immunised three times. The Hib-specific titre was measured 1 week post the second immunisation (1wp2) and 1 week post the third immunisation (1wp3).

MODES FOR CARRYING OUT THE INVENTION

Example 1

α-GalCer Suppresses the Immune Response to Saccharide Antigens

Four groups of five six-week old female mice (strain: C57BL/6) were immunized with: 1) PBS, 2) 0.1 µg of α-GalCer, 3) 3.5-10 µg of a mixture of 23 polysaccharides derived from 23 different serotypes of S. pneumoniae (Streptopur) or 4) 3.5-10 µg of Streptopur and 0.1 µg of α-GalCer. Immunisation was intramuscular in a volume of 100 µl. All four groups of mice were boosted twelve weeks later with 3.5-10 µg Streptopur. The immunisation schedule is shown in FIG. 1A.

The mice were bled 4, 8 and 12 days after priming and 4, 8 and 12 days after boosting and the levels of S. pneumoniae specific antibodies in the blood was determined by ELISA. Mice primed with Streptopur and α-GalCer showed reduced S. pneumoniae-specific antibody titres compared to mice primed with Streptopur alone (FIGS. 2 and 3), particularly after the first dose (FIG. 3A), suggesting that α-GalCer suppresses the immune response to saccharide antigens.

After 18-22 weeks, the mice were sacrificed and the number of S. pneumoniae-specific B cells in their spleens was determined by Elispot. The spleens of mice primed with α-GalCer and boosted with Streptopur also contained lower numbers of S. pneumoniae-specific B cells compared to the spleens of mice primed with PBS and boosted with Streptopur (FIG. 4). These results support the suggestion that α-GalCer suppresses the immune response to saccharide antigens.

A further experiment was conducted to assess whether the lower antibody response to S. pneumoniae polysaccharides observed in mice immunized with Streptopur and α-GalCer requires invariant Natural Killer T cells. Four groups of six-week old female mice (C57L/6 WT, CD1d+/-, CD1d-/- or JA18-/-) were immunised with: 1) PBS, 2) 0.1 µg of α-GalCer, 3) 3.5 µg of Streptopur (SP) or 4) 3.5 µg of Streptopur and 0.1 µg of α-GalCer. Immunisation was intramuscular in a volume of 50 µl. The mice were bled 4, 8 and 12 days after priming and the levels of S. pneumoniae specific antibodies in the blood was determined by ELISA. The immunisation schedule is shown in FIG. 1B.

C57L/6 wild type mice primed with Streptopur and α-GalCer showed reduced S. pneumoniae-specific antibody titres compared to CD57L/6 wild type mice primed with Streptopur alone (FIG. 8A), confirming that α-GalCer suppresses the immune response to S. pneumoniae saccharide antigens.

In contrast, there was no significant difference in S. pneumoniae-specific antibody titres in JA18-/-, CD1d-/- and CD1d-/+ mice primed with Streptopur and α-GalCer compared to JA18-/-, CD1d-/- and CD1d-/+ primed with Streptopur alone (FIG. 8B-D). These results suggest that α-Gal- Cer-induced inhibition of the response to *S. pneumoniae* saccharides requires invariant NKT cells.

*S. pneumoniae*-specific antibody titres were lower C57L/6 wild type mice primed with Streptopur alone in the absence of α-GalCer compared to antibody titres in JA218−/−, CD1d−/− and CD1d−/+ primed with Streptopur alone (FIG. 9). These results suggest that invariant NKT cells may have a negative effect on antibody responses to *S. pneumoniae* saccharides even in the absence of α-GalCer, a negative effect that is further strengthened in the presence of α-GalCer.

Further experiments have demonstrated that the suppression of the immune response to saccharide antigens by α-GalCer is also seen in mice that are between 6 and 8 weeks of age (FIG. 10).

Example 2

α-GalCer Enhances the Immune Response to Saccharide Antigen Conjugates

In contrast to the reduction in antibody titres observed when α-GalCer was administered with saccharide antigens from *S. pneumoniae* (Streptopur), administration of α-GalCer enhanced the antibody response to saccharide antigens conjugated to a carrier protein.

Mice immunised with a Hib-human serum albumin conjugate (Hib-HSA) and α-GalCer displayed considerably higher Hib-specific Ig titres than mice immunised with Hib-HSA conjugate and PBS (FIG. 11). Similarly, immunisation with a MenC-CRM conjugate and α-GalCer displayed a significant increase in MenC-specific Ig titres compared with mice immunised with a MenC-CRM conjugate and PBS (FIG. 7, immunised according to the FIG. 1C schedule).

As shown in FIG. 5, while no antibody response to MenC was ever observed in mice immunized with MenC alone, mice immunised with a MenC-CRM conjugate and α-GalCer displayed a significant increase in MenC-specific antibody titers compared with mice immunised with a MenC-CRM conjugate and PBS. Admixing α-GalCer with the conjugated enhanced the antibody response against both the saccharide and the conjugates.

Immunisation with a MenA-CRM conjugate and α-GalCer also resulted in an increase in MenA-specific Ig titres (FIG. 6). In experiments performed at the same time, however, a strong inhibitory action of α-GalCer on unconjugated MenA saccharides was not observed.

In summary, although α-GalCer can inhibit the immune response to saccharide antigens, this effect can be reversed, and the immune response to saccharide antigens can be enhanced by α-GalCer, if the saccharide antigen is conjugated to a carrier.

It will understood that the invention has been described by way of example only and modification of detail may be made without departing from the spirit and scope of the invention.

REFERENCES

[1] Natori et al, *Tetrahedron*, 1994, 50: 2771-2783
[2] EP-A-1018548
[3] Galli et al, *Vaccine*, 2003, 21: S2/48-S2/54
[4] Galli et al, *J. Exp. Med*, 2003, 197: 1051-1057
[5] WO03/009812
[6] Gonzalez-Aseguinolaza et al, *J. Exp Med*, 2002, 5: 617-624
[7] Huang et al., 2003, Abstract 396, 10th Conference on retroviruses and opportunistic infection
[8] U.S. Pat. No. 5,936,076
[9] Oki et al, *J. Clin. Investig.*, 113: 1631-1640
[10] United Kingdom patent application 0323103.2
[11] WO03/007985
[12] *Vaccine* (ed Plotkin et al) Fourth Edition ISBN 0-7216-9688-0
[13] Wessels et al. (1990) *J Clin Invest* 86:1428-33.
[14] Wessels et al. (1989) *Infect Immun* 57:1089-94.
[15] International patent application PCT/IB03/01436.
[16] Ravenscroft et al. (1999) *Vaccine* 17:2802-2816.
[17] Costantino et al. (1999) *Vaccine* 17:1251-1263.
[18] Anonymous (January 2002) Research Disclosure, 453077.
[19] Anderson (1983) *Infect Immun* 39(1):233-238.
[20] Anderson et al. (1985) *J Clin Invest* 76(1):52-59.
[21] EP-A-0372501.
[22] EP-A-0378881.
[23] EP-A-0427347.
[24] WO93/17712
[25] WO94/03208.
[26] WO98/58668.
[27] EP-A-0471177.
[28] WO91/01146.
[29] Falugi et al. (2001) *Eur J Immunol* 31:3816-3824.
[30] Baraldo et al, (2004) *Infect Immun*. 72:4884-7
[31] EP-A-0594610.
[32] WO00/56360.
[33] WO02/091998.
[34] Kuo et al. (1995) *Infect Immun* 63:2706-13.
[35] WO01/72337
[36] WO00/61761.
[37] WO99/42130.
[38] WO2004/011027.
[39] WO96/40242.
[40] Lei et al. (2000) *Dev Biol* (*Basel*) 103:259-264.
[41] WO00/38711; U.S. Pat. No. 6,146,902.
[42] Lees et al. (1996) *Vaccine* 14:190-198.
[43] WO95/08348.
[44] WO98/42721
[45] U.S. Pat. No. 4,882,317
[46] U.S. Pat. No. 4,695,624
[47] *Mol. Immunol.*, 1985, 22, 907-919
[48] EP-A-0208375
[49] WO00/10599
[50] Gever et al., Med. Microbiol. Immunol, 165: 171-288 (1979).
[51] U.S. Pat. No. 4,057,685.
[52] U.S. Pat. Nos. 4,673,574; 4,761,283; 4,808,700.
[53] U.S. Pat. No. 4,459,286.
[54] U.S. Pat. No. 4,965,338
[55] U.S. Pat. No. 4,663,160.
[56] U.S. Pat. No. 4,761,283
[57] U.S. Pat. No. 4,356,170
[58] Lei et al. (2000) *Dev Biol* (*Basel*) 103:259-264.
[59] WO00/38711; U.S. Pat. No. 6,146,902.
[60] WO99/24578.
[61] WO99/36544.
[62] WO99/57280.
[63] WO00/22430.
[64] Tettelin et al. (2000) *Science* 287:1809-1815.
[65] WO96/29412.
[66] Pizza et al. (2000) *Science* 287:1816-1820.
[67] WO01/52885.
[68] Bjune et al. (1991) *Lancet* 338(8775):1093-1096.
[69] Fukasawa et al. (1999) *Vaccine* 17:2951-2958.
[70] Rosenqvist et al. (1998) *Dev. Biol. Stand.* 92:323-333.
{71} WO02/22167.
[72] Bell (2000) *Pediatr Infect Dis J* 19:1187-1188.

[73] Iwarson (1995) *APMIS* 103:321-326.
[74] Gerlich et al. (1990) *Vaccine* 8 Suppl:S63-68 & 79-80.
[75] Hsu et al. (1999) *Clin Liver Dis* 3:901-915.
[76] Gustafsson et al. (1996) *N. Engl. J. Med.* 334:349-355.
[77] Rappuoli et al. (1991) *TIBTECH* 9:232-238.
[78] *Vaccines* (2004) eds. Plotkin & Orenstein. ISBN 0-7216-9688-0.
[79] WO02/02606.
[80] Kalman et al. (1999) *Nature Genetics* 21:385-389.
[81] Read et al. (2000) *Nucleic Acids Res* 28:1397-406.
[82] Shirai et al. (2000) *J. Infect. Dis.* 181(Suppl 3):S524-S527.
[83] WO99/27105.
[84] WO00/27994.
[85] WO00/37494.
[86] WO99/28475.
[87] Ross et al. (2001) *Vaccine* 19:4135-4142.
[88] Sutter et al. (2000) *Pediatr Clin North Am* 47:287-308.
[89] Zimmerman & Spann (1999) *Am Fam Physician* 59:113-118, 125-126.
[90] Dreesen (1997) *Vaccine* 15 Suppl:S2-6.
[91] *MMWR Morb Mortal Wkly Rep* 1998 Jan. 16; 47(1):12, 19.
[92] Covacci & Rappuoli (2000) *J. Exp. Med.* 19:587-592.
[93] WO93/18150.
[94] Covacci et al. (1993) *Proc. Natl. Acad. Sci. USA* 90:5791-5795.
[95] Tummuru et al. (1994) *Infect. Immun.* 61:1799-1809.
[96] Marchetti et al. (1998) *Vaccine* 16:33-37.
[97] Telford et al. (1994) *J. Exp. Med.* 179:1653-1658.
[98] Evans et al. (1995) *Gene* 153:123-127.
[99] WO96/01272 & WO96/01273, especially SEQ ID NO:6.
[100] WO97/25429.
[101] WO98/04702.
[102] McMichael (2000) *Vaccine* 19 Suppl 1:S101-107.
[103] Schuchat (1999) *Lancet* 353(9146):51-6.
[104] WO02/34771.
[105] Dale (1999) *Infect Dis Clin North Am* 13:227-43, viii.
[106] Ferretti et al. (2001) *PNAS USA* 98: 4658-4663.
{107} Kuroda et al. (2001) *Lancet* 357(9264):1225-1240; see also pages 1218-1219.
[108] Anderson (2000) *Vaccine* 19 Suppl 1:S59-65.
[109] Kahn (2000) *Curr Opin Pediatr* 12:257-262.
[110] Crowe (1995) *Vaccine* 13:415-421.
[111] *J Toxicol Clin Toxicol* (2001) 39:85-100.
[112] Demicheli et al. (1998) *Vaccine* 16:880-884.
[113] Stepanov et al. (1996) *J Biotechnol* 44:155-160.
[114] Charalambous & Feavers (2001) *J Med Microbiol* 50:937-939.
[115] WO00/56365.
[116] Gennaro (2000) *Remington: The Science and Practice of Pharmacy*. 20th ed ISBN: 0683306472
[117] *Vaccine Design . . .* (1995) eds. Powell & Newman. ISBN: 030644867X. Plenum.
[118] WO00/23105.
[119] WO90/14837.
[120] U.S. Pat. No. 5,057,540.
[121] WO96/33739.
[122] EP-A-0109942.
[123] WO96/11711.
[124] WO00/07621.
[125] Barr et al. (1998) *Advanced Drug Delivery Reviews* 32:247-271.
[126] Sjolanderet et al. (1998) *Advanced Drug Delivery Reviews* 32:321-338.
[127] Niikura et al. (2002) *Virology* 293:273-280.
[128] Lenz et al. (2001) *J Immunol* 166:5346-5355.
[129] Pinto et al. (2003) *J Infect Dis* 188:327-338.
[130] Gerber et al. (2001) *Virol* 75:4752-4760.
[131] WO03/024480
[132] WO03/024481
[133] Gluck et al. (2002) *Vaccine* 20:B10-B16.
[134] EP-A-0689454.
[135] Johnson et al. (1999) *Bioorg Med Chem Lett* 9:2273-2278.
[136] Evans et al. (2003) *Expert Rev Vaccines* 2:219-229.
[137] Meraldi et al. (2003) *Vaccine* 21:2485-2491.
[138] Pajak et al. (2003) *Vaccine* 21:836-842.
[139] Kandimalla et al. (2003) *Nucleic Acids Research* 31:2393-2400.
[140] WO02/26757.
[141] WO99/62923.
[142] Krieg (2003) *Nature Medicine* 9:831-835.
[143] McCluskie et al. (2002) *FEMS Immunology and Medical Microbiology* 32:179-185.
[144] WO98/40100.
[145] U.S. Pat. No. 6,207,646.
[146] U.S. Pat. No. 6,239,116.
[147] U.S. Pat. No. 6,429,199.
[148] Kandimalla et al. (2003) *Biochemical Society Transactions* 31 (part 3):654-658.
[149] Blackwell et al. (2003) *J Immunol* 170:4061-4068.
[150] Krieg (2002) *Trends Immunol* 23:64-65.
[151] WO01/95935.
[152] Kandimalla et al. (2003) *BBRC* 306:948-953.
[153] Bhagat et al. (2003) *BBRC* 300:853-861.
[154] WO03/035836.
[155] WO95/17211.
[156] WO98/42375.
[157] Beignon et al. (2002) *Infect Immun* 70:3012-3019.
[158] Pizza et al. (2001) *Vaccine* 19:2534-2541.
[159] Pizza et al. (2000) *Int J Med Microbiol* 290:455-461.
[160] Scharton-Kersten et al. (2000) *Infect Immun* 68:5306-5313.
[161] Ryan et al. (1999) *Infect Immun* 67:6270-6280.
[162] Partidos et al. (1999) *Immunol Lett* 67:209-216.
[163] Peppoloni et al. (2003) *Expert Rev Vaccines* 2:285-293.
[164] Pine et al. (2002) *J Control Release* 85:263-270.
[165] Domenighini et al. (1995) *Mol Microbiol* 15:1165-1167.
[166] WO99/40936.
[167] WO99/44636.
[168] Singh et al] (2001) *J Cont Release* 70:267-276.
[169] WO99/27960.
[170] U.S. Pat. No. 6,090,406
[171] U.S. Pat. No. 5,916,588
[172] EP-A-0626169.
[173] WO99/52549.
[174] WO01/21207.
[175] WO01/21152.
[176] Andrianov et al. (1998) *Biomaterials* 19:109-115.
[177] Payne et al. (1998) *Adv Drug Delivery Review* 31:185-196.
[178] Stanley (2002) *Clin Exp Dermatol* 27:571-577.
[179] Jones (2003) *Curr Opin Investig Drugs* 4:214-218.
[180] WO99/11241.
[181] WO94/00153.
[182] WO98/57659.
[183] European patent applications 0835318, 0735898 and 0761231.
[184] WO98/20734.
[185] WO03/009869
[186] WO01/30390.

The invention claimed is:

1. A composition comprising: (a) an immunologically effective amount of a saccharide antigen that is conjugated to a carrier; and (b) an α-glycosylceramide adjuvant.

2. The composition of claim 1 wherein the α-glycosylceramide adjuvant is an α-galactosylceramide.

3. The composition of claim 2 wherein the α-galactosylceramide is (2S,3S,4R)-1-O-(α-D-galactopyranosyl)-2-(N-hexacosanoylamino)-1,3,4-octadecanetriol.

4. The composition of any one of claims 1-3 wherein the saccharide antigen is a bacterial capsular saccharide.

5. The composition of claim 4 wherein the bacterial capsular saccharide is from *Neisseria meningitidis, Haeomophilus influenzae* or *Streptococcus pneumoniae*.

6. The composition of claim 1 comprising more than one saccharide conjugate.

7. The composition of claim 1 wherein the carrier is a protein.

8. The composition of claim 1 wherein the carrier is a bacterial toxin.

9. A kit comprising: (a) an immunologically effective amount of a saccharide antigen that is conjugated to a carrier; and (b) an α-glycosylceramide adjuvant.

10. The composition of claim 8 wherein the bacterial toxin is diphtheria toxoid or tetanus toxoid.

11. The composition of claim 4, wherein the bacterial capsular saccharide is from *Neisseria meningitidis* serogroup A or *Neisseria meningitidis* serogroup C.

* * * * *